Figure 1:
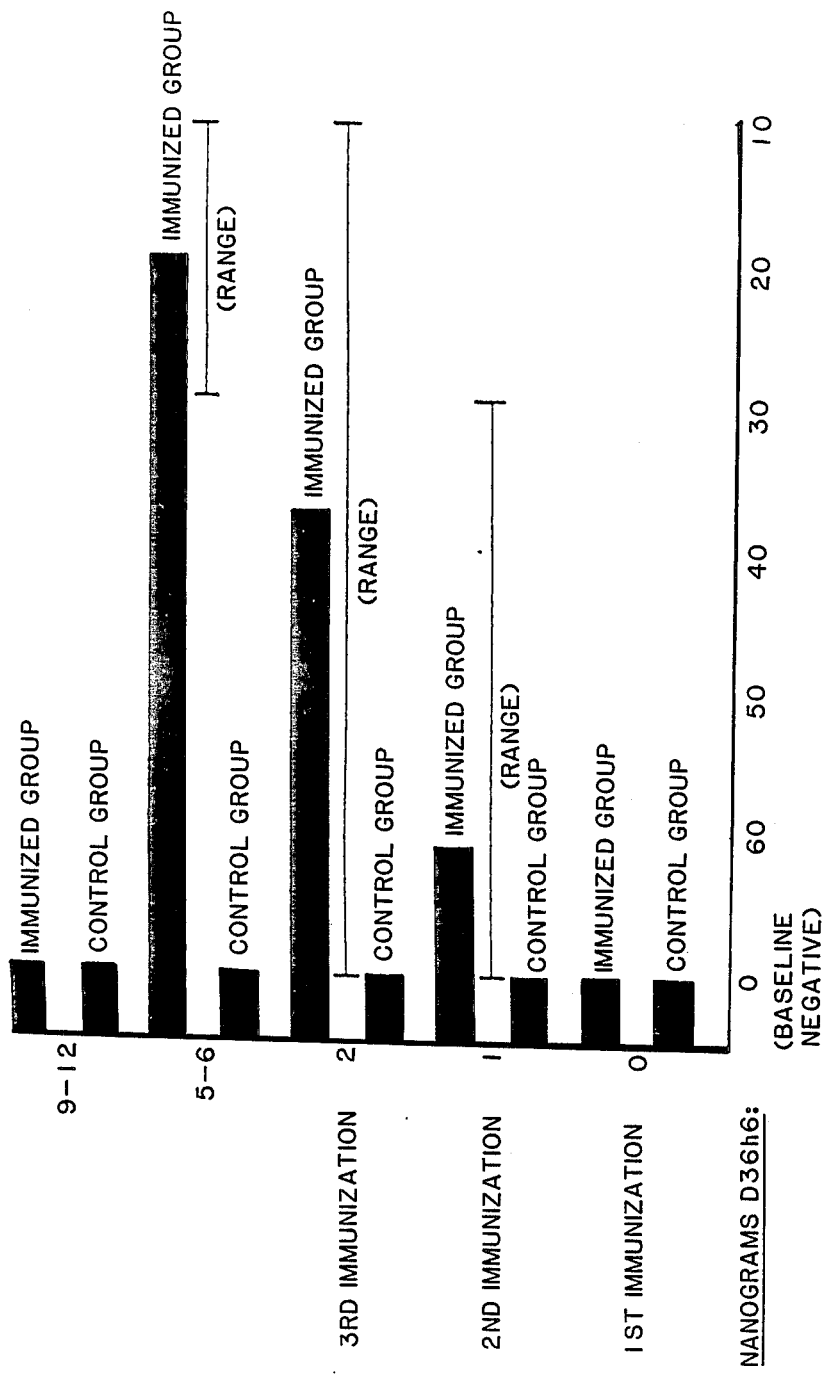

United States Patent [19]

Hollinshead

[11] Patent Number: 4,810,781
[45] Date of Patent: Mar. 7, 1989

[54] METHODS OF PREPARING EPITOPES OF TUMOR ASSOCIATED ANTIGENS

[75] Inventor: Ariel C. Hollinshead, Washington, D.C.

[73] Assignee: The George Washington University, Washington, D.C.

[21] Appl. No.: 106,817

[22] Filed: Oct. 13, 1987

Related U.S. Application Data

[62] Division of Ser. No. 003,711, Jan. 15, 1987, abandoned.

[51] Int. Cl.[4] ........................ C07K 1/12; C07K 1/14; C07K 3/28; C12Q 21/6
[52] U.S. Cl. ................... 530/413; 530/387; 530/806; 530/828; 530/808; 530/415; 530/416; 530/407; 530/403; 435/212
[58] Field of Search ............ 435/68, 69, 212; 530/413, 427, 403, 407, 806, 828, 808, 415, 416

[56] References Cited

U.S. PATENT DOCUMENTS 4,732,852  3/1988  Cohen et al. ................. 530/413

*Primary Examiner*—Delbert R. Phillips
*Assistant Examiner*—Jeff P. Kushan
*Attorney, Agent, or Firm*—Watson, Cole, Grindle & Watson

[57] ABSTRACT

Methods are disclosed for preparing (1) a pure, biologically active, immunogenic tumor-associated antigen by forming a soluble pool of membrane proteins from antigenic tissue and, by separating, identifying and characterizing antigenic and/or immunogenic proteins therefrom; (2) an ultrapure, biologically active TAA by further subjecting the pure TAA to isotachophoresis and/or affinity chromatography; and (3) making an epitope from purified TAA by injecting TAA into a host animal to stimulate the production by lymphocytes of antibodies specific to TAA, forming hybridomas capable of secreting monoclonal antibodies reactive with the TAA, dividing the TAA into fragments including epitopes, forming epitope-monoclonal antibody complexes, separating the complexes to recover the epitopes, and thereafter identifying and characterizing the epitopes.

8 Claims, 2 Drawing Sheets

METHODS OF PREPARING EPITOPES OF TUMOR ASSOCIATED ANTIGENS

This application is a divisional application of application Ser. No. 003,711, filed Jan. 15, 1987, abandoned.

Tumor-associated antigens (TAA) are polypeptides which are purified from proteins separated from the isolated, washed cell membranes of cancer cells, and which are carefully identified and characterized for their ability to produce cell-mediated immune reactions to the tumor associated antigen (TAA) by the tumor-bearing host, both by in vitro and in vivo testing. These are designed for testing as specific active immunotherapeutic or immunoprophylactic biologic drugs both for safety and for efficacy in the treatment of human cancer or for further purification and use in producing a hybridoma cell line of antibodies recognizing the tumor-associated antigen. The present invention relates to the preparation of such tumor associated antigens and epitopes therefrom.

BACKGROUND OF THE INVENTION

An initial disclosure of TAA's was made in an application for two Damon Runyon grants in 1962, and resulted in a grant award on Jan. 1, 1963 as Damon Runyon Grants 722 and 723 to the applicant as principal investigator through the Office of Sponsored Research, The George Washington University. This early work was performed in animal models, first using cancer cells in tissue culture and their growth in a privileged immunological site in Syrian hamster cheek pouches. The identification of membrane components separated from the rest of the cell and their effect in reducing the size and the number of tumors was the first report of its kind in the worldwide literature. There followed a group of studies, first on randombred hamsters with transplantable adenovirus type 12-induced tumors in which the separated, identified, soluble tumor-specific transplantation antigens derived from the soluble materials of separated tumor cell membranes showed a strong, titration-dilution curve effect in blocking tumor growth. This work was presented first at an international conference in 1967, followed by a series of published papers, first on randombred and later repeated by another institution, in cooperation with the inventor, in inbred hamsters. These studies with virus-induced tumors were then repeated by yet another institution, in cooperation with the applicant, using carcinogen-induced tumors in inbred mice. Concomitant research began in 1965 through 1968 on laboratory separation and identification studies of human cell membrane components in specific developing embryonic and fetal tissue cells, adult normal tissue cells and benign disease adult tissue cells of humans so as to further understand the distribution of normal cell membrane components, tissue antigens. The methods used in the initial work on the human HeLa cell-hamster cheek pouch model, the adenovirus-tumor hamster model and the carcinogen-induced mouse model were further perfected and established as the basis for these studies of human non-malignant tissues. These studies were then followed by studies of the cell membrane components of tumors of the same, counterpart organ. Tumor-associated antigens were separated, characterized and tested for characteristic activity and recorded as quantitatively or qualitatively unique. One such study was reported for colon cancer TAA at a 1968 Gordon Conference, with subsequent publication of these observations in Lancet in 1970, with appropriate standards and controls. Controls consisted of 1st, 2nd and 3rd trimester fetal, and adult normal and benign cell membrane soluble, separated proteins as well as TAA produced by different human tumors, thus permitting cross-reaction and comparison studies of organ-related tumor associations.

A major initial criterion involved controlled clinical evaluations of the ability of TAA to induce both allogeneic and autologous delayed hypersensitivity reactions in appropriate, related-for-cancer-type nonanergic cancer patients with primary tumors, both pre- and post-surgery. This major criterion continued to be the basis for a series of studies of different selected human cancer TAAs, along with other appropriate assays and techniques suitable for a general application or for a particular TAA, with newer methods continually assessed for application. These studies permitted evaluations of hundreds of individual fresh tissues and tumors, and allowed in vitro and in vivo comparisons and the development of preliminary clinical studies and clinical protocols for evaluation of appropriate immunogenic activities of purified TAAs.

In 1976 early results from a lumg cancer immunotherapy study were reported to the New York Academy of Science, suggesting the possibility that TAAs might be capable of producing effective, long-lasting cell-mediated immunity in the human host. There followed other clinical studies of candidate TAAs for other forms of cancer. Statistical proof of the existence of TAAs which produce cell-mediated immune reactions which are effective in the host could not be established until phase I studies for safety and phase II and III studies for efficacy were completed. In late 1986, such proof became available for lung cancer TAAs, and it is now possible to claim the existence of TAAs that produce cell-mediated immune reactions which are effective in the treatment of human cancer, thus verifying the methods and approaches used for the production of pure TAA and ultrapure TAA and epitopes therefrom. In 1980, the development of TAA monoclonal antibodies began, with a view to further understanding the TAAs. These ongoing studies, so far, have indicated the superiority of a further development, namely, the monoclonal antibody-derived epitopes of TAA selected among active antigenic determinants. Research results thus far indicate that enzyme immunoassays measuring antibodies in patient sera to TAA or to TAA monoclonal antibody-derived epitopes display superior superficity and greater utility than enzyme immunoassays using TAA monoclonal antibodies to monitor patient sera. The entirety of the sequence of methods thus far utilized for preparing TAA epitopes with these properties are described herein. References above to the work of applicant are not intended as an admission that such work constitutes prior art under U.S. law.

It is important to the art that tumor associated antigens be isolated in a pure but also active form, which degree of purity is referred to herein as "pure" for use in immunotherapy, and "ultrapure" for use in characterization, identification and for epitope preparation. Pure TAA's are obviously superior to less pure TAA's where utilized for their ability to produce cell-mediated immune reactions to the TAA. A particular use of ultrapure TAA that has been utilized by the applicant is in the production of hybridoma cell lines to obtain monoclonal antibodies for use in preparing tumor-associated antigen epitopes, which are useful as monitors of specific active immunotherapy, for measuring specific antibody responses in patients undergoing immunotherapy.

SUMMARY OF THE INVENTION

So far as the present invention is directed to a method of making a pure TAA, that pure tumor associated antigen must be biologically active and immunogenic. It is formed from immunogenic tissue, in that the antigen is capable of producing cell-mediated immune reactions in a tumor-bearing host. Broadly, the method comprises dispersing the antigenic tissue in an aqueous medium to obtain a suspension of membrane material, solubilizing the suspension, separating the solubilized suspension into membranous solids and a supernatant comprising a soluble pool of membrane solids, and separating the soluble pool into its protein components while maintaining the antigenic activity of the materials intact. Thereafter, the antigenic protein moiety is identified and characterized.

This method of preparing a pure, biologically active, immunogenic TAA is subject to narrower definitions. In particular, the suspension is preferably solubilized by subjecting it to sonication in a sonic oscillator. The soluble pool is separated into its protein components while maintaining antigenic activity by one or, more preferably, several of the following method steps: (1) according to size by ultrafiltration chromatography; (2) according to charge by polyacrylamide gel electrophoresis, (3) according to charge by ion exchange chromatography, and (4) according to affinity for monospecific or monoclonal antibodies by affinity chromatography.

Identification and characterization of the antigenic protein moiety is carried out by one or, preferably, more or all of the following methods: (1) by polyacrylamide gel electrophoresis including the use of SDS-PAGE gel staining and comparison of densitometry profiles in gel separations, as well as migration in relation to control proteins of known molecular weight determined by reactions with monospecific antisera in gel double diffusion, (2) by immuno-diffusion, immuno-electrophoresis against a battery of hyperimmune and immune and control sera and prepared monospecific and monoclonal antibodies; (3) by specific lymphocyte stimulation assays; (4) by delayed hypersensitivity reaction skin testing in titration assays, (5) by enzyme immunoassays to characterize tumor-associated antigens using tumor-related and control sera; (6) by testing of stability at various temperatures and times at said temperatures; (7) by isotope tagging of TAA antibodies to show localization in tumors, and (8) by indirect immunofluorescence studies of cancer tissues, cells or subsets thereof to TAA antibodies. It is considered most preferable that at least methods (1), (2), (4), (5) and (6) be utilized in combination, although all eight methods may be so used where appropriate.

As so defined, pure tumor associated antigen has been produced, identified and characterized. That pure TAA may be further purified to what is here defined as an ultrapure state. The method of producing such ultrapure TAA comprises subjecting pure TAA to isotachophoresis. Another method is affinity chromatography in which purification is carried out by utilizing the affinity of monospecific or monoclonal antibodies for the antigen.

Thereafter, the pure, or, more preferably, ultrapure tumor associated antigen is used as the starting material to form epitopes thereof. Such starting materials are TAAs of proven efficacy in generating cell-mediated immune reactions appropriate for use in clinical application as immunotherapeutics. In addition, such epitopes are particularly well adapted to monitor a patient's response to immunotherapy to determine whether patients are producing antibodies to combat specific tumors.

To make an epitope from a tumor associated antigen, which epitope is capable of generating a specific immunotherapeutic response, a broad technique utilized comprises injecting the TAA, and preferably ultrapure TAA, in a host animal to stimulate the production by lymphocytes of the animal of antibodies specific to the TAA. Those lymphocytes are fused with an immortal cell line to form hybridomas capable of secreting selected monoclonal antibodies reactive with the TAA, and those antibodies, which may be abbreviated as Mabs, are coated on suitable beads for affinity chromatography. The Mabs are stably bonded to these beads so that when the TAAs, initially injected into the host animal, are mixed with the Mab-conjugated beads, high affinity TAA-Mab complexes are formed which are insoluble in a neutral aqueous medium.

After the TAA-Mab complexes have been formed, washes are carried out to remove unbound materials, e.g., materials other than the complexes. The TAAs are then recovered from the Mab-conjugated beads, in one manner by being washed with an acidic solution which dissociates the TAAs from the bound Mabs. After such washing, the TAAs formerly bound as part of the complex are recovered and then fragmented to produce smaller constituents, which include epitopes having specific reactivity with the monoclonal antibodies. This can be achieved in a variety of ways, including enzyme digestion. Thereafter, the TAA fragments are again mixed with the Mab-conjugated beads and those fragments (epitopes) with antigenic activity will complex with the Mabs bound to the beads. Thereafter, the beads are washed once again to remove all TAA fragments that did not complex with the bound Mab; the epitope-Mab complex is separated, preferably by pH manipulation, whereupon the epitope is washed from the Mabs and recovered. In this manner epitopes are obtained as a final product. The epitopes are capable of reacting with monoclonal antibodies which have the ability to bind to the TAA. These epitopes represent only a small fraction of the entire TAA molecule, and because of their substantially diminished size, can be used not only therapeutically, but as a monitor in reaction tests to determine whether a patient under treatment is generating a sufficient immune response in vivo so that indicia of reactivity will be noted when the epitopes are studied by enzyme immunoassay using sera from patients.

These and other objects, features and advantages of the present invention in its several forms will be more apparent when taken in connection with the following, detailed description of preferred embodiments of the invention, which detailed descriptions are are accompanied by several figures and tables all of which served to illustrate the invention to those of skill in the art.

SEPARATION, IDENTIFICATION, PURIFICATION AND ANALYSIS OF ANTIGENS

Specimens of cancer tissue, control tissue material, and tissue culture cell lines are prepared as follows. The cancer or control tissue is, upon receipt in the laboratory, immediately minced in physiological saline, washed several times, and the cells separated by the use of 60-mesh stainless steel sieves and by aspiration through a wide-bore 5-ml pipette. In this procedure, as in all procedures to follow, sterility is monitored by placing a drop of the appropriate material on both blood-agar and thioglycolate. The dispersed, single cell suspension is counted in four chambers or two hemocytometers; three counts of the cells are made using white blood cell diluent, trypan blue, and neutral red, and viable cell count is determined. The single cell suspension is then frozen ($-70°$ C.) and thawed, and isotonic to hypotonic saline membrane extraction is performed using a modified Davies procedure. The single cell suspension is centrifuged for 10 minutes at 2,500 rpm in an IEC low speed, refrigerated centrifuge and the supernatant retained. The pellet is resuspended in 10:1 (v/v) and again centrifuged at 2,500 rpm. This resuspension and those following are carried out twice at each molar concentration: 0.07M NaCl and 0.00M NaCl. Supernatants are retained at each step, pooled, and centrifuged in a Beckman L3-50 Ultracentrifuge at 100,000×g. The supernatant is discarded, and the pellet of membrane material is washed from the tubes and resuspended in physiological saline. Membrane protein is measured at this point by the Lowry method. The material is examined by electron microscopy to assess the membrane pieces and the lack of nuclear material. In addition HLA determination of whole cells and membranes are made by the chromium release cytotoxicity method 22 using a broadly reactive serum, so that quantitation of membrane components can be calculated prior to further study.

The suspension of membrane material is then subjected to sequential low frequency (9 kc/sec) sonication in a Raytheon model DF-101 Sonic Oscillator. Centrifugation with retention of the supernatant and resuspension of the membrane pellet is carried out for one hour at 100,000×g after each interval sonication period: the sonication periods consist of 3 min., 4½ min., and 6 min. for respective progressive intervals. The supernatants are pooled and termed the soluble pool of membrane protein, and a Lowry protein determination is made. This soluble pool is then concentrated by Diaflo ultrafiltration (Amicon). The sample is then subjected to one or more methods of separation as follows.

Sephadex G-200 columns are prepared to accommodate the amount of protein obtained. The columns are washed with 0.01M phosphate buffer for several hours and the void volume determined using Dextran blue. The next day, the soluble sonicates are separated over Sephadex gels, 2 ml fractions collected, and the profile recorded at 220 and 280 mu. Fractions are pooled according to protein peaks, and the pools concentrated by Diaflo ultrafiltration. In all of these steps, the materials are kept at 0° or 4° C. Standard proteins are separated on identical columns for molecular weight calculations. The following day, any concentrations which were not accomplished the previous day are completed, and all of the material tested by the Lowry procedure for protein content. Each fraction is either diluted or further concentrated in order to have fractions of required protein content for further study. Sephadex fractions are analyzed and the appropriate material aliquoted for immunization after in vitro and in vivo analyses. Examples of cancer fractions are shown in Table 1.

TABLE 1

$$K_{AV} = \frac{Ve - Vo}{Vt - Vo}$$

| | |
|---|---|
| lung cancer II and III | Squamous .105 → 1.000 |
| | Adeno .149(±.008) → 1.00 |
| | Undifferentiated .099(±.008) → 1.00 |
| melanoma Ib | .116(±0.013) → .263(±0.020) |
| bladder cancer II | .315 → .682 |
| colon cancer Ib and IIa | .115(±.031) → .515(±.061) |
| ovarian cancer II | .223 → .380 |

1. Chromatographic reproducibility between batches is insured by monitoring the fractions in every batch by gelelectrophoresis.
2. The exact definitions of each peak - see table above.
3. Criteria for a successful separation is the presence of appropriate bands in stained polyacrylamide gels and skin test positivity in nonanergic patients and if possible, previously positive to earlier lots.
4. Pooled fractions should be expressed as an inclusive range of $K_d$ values. "Since $v_t - V_o$ includes the volume of the gel forming substance, which is inaccessible to all solute molecules, $K_{AV}$ is not a true partition coefficient. However, for a given gel there is a constant ratio of $K_{AV}:K_d$ which is independent of the nature of the solute or its concentration. $K_{AV}$ is easily determined and, like $K_d$, defines solute behavior independently of the bed dimensions and packing." (Pharmacia Fine Chemicals Product Guide, 1980)

Storage at $-70°$ C. is crucial in maintaining activity of the antigen preparation. Separate equipment and separate hoods are used for handling normal tissues. An example of Sephadex separation and recovery is given for hypernephroma TAA is presented in the following Example 1.

EXAMPLE 1

A well-defined hypernephroma tumor, about the size of a man's fist (200 grams) yields approximately 2.002 grams of cell membranes in 50 milliliter solution (a concentration of 4.004 milligrams per 0.1 ml). When said membranes are subjected to low frequency sonication by gentle stepwise methods, a soluble pool of 488.1 milligrams protein, by the Lowry method, are obtained in 190 milliliters (256.9 micrograms per 0.1 milliliters). These are then aliquoted into 19 tubes of approximately 10 milliliters each containing 25.69 milligrams per tube. At this point polyacrylamide gel electrophoresis (PAGE) is performed using stains for carbohydrates (PAS stain), for lipids (ORO stain) and for protein (CBB stain) and densitometry profiles are also done on these stepwise, gradient density polyacrylamide gel electrophoresis separations. In this particular separation, 377.13 milligrams of soluble pool were put aside for another separation at a later date.

In this particular separation, 27 Sephadex G-200 columns were run, using 4.11 milligrams per 1.6 ml each (110.97 milligrams total), and the total were collected in fractions. The total of this separation was such that the elution volume, the elution volume over the void volume, and the total recovery were as follows:

| COLLECTION | ELUTION VOLUME | Ve/Vo | RECOVERY (mg protein): |
|---|---|---|---|
| VO: | 30.25 ml | | |
| Fx I: | 10.7 ml | 0.3537 | 3.8399 mg |
| Fx II A: | 17.0 ml | 0.56198 | 3.2384 mg |
| Fx II B: | 27.5 ml | 0.90909 | 5.3824 mg |
| Fx III: | 27.8 | 0.9190 | 1.7300 mg |

Skin test syringes were prepared in sets, so that approximately 80 to 110 micrograms of protein was present in test material:

Fx I: 82.5 mcg/0.1 ml each
Fx II A: 105.6 mcg/0.1 ml each
Fx II B: 109.1 mcg/0.1 ml each Fx III: 100 mcg/0.1 ml each.

Appropriate skin testing was performed in order to identify those fractions with activity. In addition lymphocytes were removed from a patient with hypernephroma and specific lymphocyte stimulation assays were performed (see later description LS Assay). Activity was identified both in fractions IIA and IIB. The purpose of this example is to describe the initial separation steps and procedures. At this point, soluble pool from a normal counterpart organ obtained previously from a traffic accident victim by sterile procedure at autopsy, was separated in a similar manner in order to compare fraction IIA (100.5 mcg/0.1 ml) and IIB (108 mcg/0.1 ml) with that obtained from the tumor specimen. Individual tumor gel PAGE bands were separated initially by slicing gels and eluting bands and retesting for appropriate separation. The concentrated proteins of separated gel bands were then tested at equal protein concentrations for their ability to produce cell-mediated immune reactivity. Hyperimmune antisera were prepared against active antigens.

While the hyperimmune antiserum was under production, other methods of separation of candidate antigens were tested to see whether or not ion exchange chromatography, or ultragradient or other separation methods might be superior. Stability of the separated proteins was tested at various temperatures. Immunodiffusion-immunoelectrophoresis of antigens was eventually tested against the hyperimmune sera produced as well as against sera from tumor-bearing patients. These and other studies are described in subsequent examples using other types of cancer. Sterility testing and good laboratory practices were adhered to in all protocols. The final product selected for use in immunotherapy was, eventually, fractions IIA+IIB, and the ideal vaccination concentration was set at approximately 500 milligrams per immunization. The above figures will permit calculations of loss and recovery, and give an idea of loss and recovery for a given tumor. These losses and recoveries vary depending upon the type of tumor under study.

Analysis of material and further purification for analytic studies are by gradient polyacrylamide (discontinuous) gel electrophoresis procedures which have been described. The apparatus which we employ is not available from any one company, since our methodology requires a different combination of power source and gel bath. A 1:1:2 gel solution is made by mixing gel buffer, distilled water, and the appropriate gel solution. This mixture is added to and mixed with an equal volume of the ammonium persulfate solution immediately before preparing the column. This final catalyzed solution is then layered with a flat end 23 ga needle into the gel tubes as follows, the gel tubes having been immersed in a 1:200 dilution of Kodak Photo Flow 200 and air dried prior to use. 10 or 12%, 7%, 4.75% and 3.5% gel solution are layered carefully to avoid mixing. Distilled water is layered onto the 3.5% gel to the top of the tube (12 cm) to allow polymerization. This water is removed by shaking prior to use. At least 40 minutes must be allowed for complete polymerization. Greater reproducibility is obtained if the gels are allowed to age more than 12 hrs. See Table 2 for gel stock solutions and procedure outline.

TABLE 2

| Stock Solutions for Polyacrylamide Gel Electrophoresis | | |
|---|---|---|
| Buffer A pH 8.9 | | Prepare fresh |
| 48 ml 1 N HCl | | every week |
| 36.6 gm THAM (tris [hydroxymethy 1] amino methane) | | |
| 0.23 ml TEMED (N,N,N',N'—tetramethylethylenediamine) | | |
| Add distilled water to 100 ml and filter | | |
| solutions | | |
| 12% | 46.9 gm acrylamide | Prepare fresh |
| | 0.95 gm Bis (N,N'—methylene-bisacrylamide) | every two weeks |
| 10% | 39.2 gm acrylamide | |
| | 0.80 gm bis | |
| 7% | 28.0 gm acrylamide | |
| | 0.70 gm bis | |
| 4.75% | 18.6 gm acrylamide | |
| | 0.40 gm bis | |
| 3.5% | 13.85 gm acrylamide | |
| | 0.15 gm bis | |
| Add distilled water to 100 ml and filter | | |
| Chamber buffer pH 8.3 (10 ×) | | |
| THAM 6.0 gm | | |
| Glycine 28.8 gm | | |
| Add distilled water to 1000 ml and filter | | |
| (dilute 1:10 in distilled water before use) | | |
| Ammonium persulfate | | |
| 0.14 gm ammonium persulfate | | |
| Add distilled water to 100 ml and filter | | |
| Protein stain (Coomassie Brilliant Blue R250) (0.05% CBB in 20% trichloroacetic acid) | | Prepare fresh every week |
| 0.25 gm CBB | | |
| 100 gm TCA | | |
| Add distilled water to 500 ml | | |
| Filter through Whatman #5 | | |
| Procedure for gel preparation | | |
| Soak gel tubes in distilled water containing 1:200 Kodak Photo-Flo solution | | |
| Air dry, seal bottoms with parafilm, set up vertically | | |
| Prepare gel solutions | | |
| (1 part H₂O, 1 part gel buffer A, 2 parts working gel) | | |
| Mix equal volumes of gel preparation and ammonium persulfate. Aliquot in layers | | |
| (Solutions must be at room temperature when aliquoting) | | |

Prepared gels are placed in the upper chamber grommets of a Canalco Model long bath. The upper and lower chambers of the bath are then filled with chamber buffer, insuring that air bubbles are removed from the loading section of the gel tube (upper (−) portion). A drop of tracking dye (Bromphenol Blue in NaOH at pH 8.3) is added to the upper chamber to follow the course of migration of the leading ion front. A few grains of sucrose are added to the sample to insure that it is heavier than the chamber buffer. The chamber is then carefully loaded onto the top of the 3.5% gel by means of a Hamilton microliter glass syringe. Electrophoresis is carried out using a Buchler Model 301155 Voltage and Current regulated power supply in the constant current mode. 4 ma are applied to each column, and the gel run takes 75–80 minutes.

As loaded, the preferred gel length is 10 cm,, in a tube with an I.D. of 0.5 cm. The lower 6 cm of the tube is loaded with the 10–12% gel. Layered on that gel are, in order, 1.5 cm of 7% gel, 1 cm of 4.75% gel, and 1.5 cm of 3.5% gel. The remaining uppermost 1 cm or so of the tube is unfilled.

After the run, gels are removed from their tubes by means of rimming with a finely tapered needle with injection of water between the gel and the tube wall as needed. The gels are then ready for staining or for cutting and eluting protein from appropriate regions. Some of the stains employed are Coomassie Brilliant Blue, non-specific protein stain; Oil Red O, lipoprotein stain, and Periodic Acid Schiff stain, a carbohydrate stain.

Accurate drawings are made and photographs are taken during every study.

To prepare material for careful analysis, soluble sonicate of appropriate samples at a level of approximately 100 ug/0.1 ml are stained as a reference for further separation. Relative concentration of TAA to total soluble membrane protein is quantitated by scanning gels at 610 nm on a Gelman ACD-15 densitometer. Densitometry tracings are filed for every study, and used for experimental comparisons, with tracings of soluble cell membrane components from normal adult and 1st, 2nd, 3rd trimester fetal cells of the counterpart tissue as well as for comparisons with benign, primary and metastatic tumors of that tissue and for cross-comparisons with other preparations. Unstained gels are then sliced for precise regions. Gels are eluted with sterile saline at 4° C. for 50 hours, concentrated by ultrafiltration, rediluted 100 fold, and reconcentrated in order to help eliminate any toxic dialyzable substances. These materials are used for skin testing, without side effects, and are also used for ovarian cancer therapy. Soluble gel components are also cross-tested by enzyme immunoassay against a battery of antisera to known or putative early and late viral components associated with animal cancers and are also evaluated for hormonal or enzymatic properties. With these methods, recovery of material previously separated by Sephadex is often between 50 and 100%; and since even amounts to 100 ug protein are applied to each column, a fairly uniform amount of protein is recovered for testing purposes, thus assuring a more standard preparation for cross-testing and for comparisons of several tests. The bands obtained from the different preparations may be studied for their molecular weight determination, first by migration in SDS polyacrylamide gels in comparison with known standard curves of elution of known proteins.

EXAMPLE 2

An example of pure TAA obtained by this method is ovarian TAA which is gel region 3. This form of separation used 292 preparative gel tubes with sample size of 1.5 mg in 0.6 ml ovarian cancer cell membrane sonicate, or Sephadex fraction II, per tube with a current of 12 mA per tube and a length of run of 5 hours. Region 3 is measured from the tracking dye with adjustment for ratio of tracking dye to albumin and was approximately 5.04 to 6.3 cm for lower and upper cuts. Elution was for 4 days at 5° C. in normal saline. Total recovery was approximately 24% of total protein loaded.

The appropriate separation of pure TAAs which produce cell-mediated reactions varies with the cancer type. Examples of pure TAA are Sephadex fractions for lung cancer II and III, melanoma Ib, hypernephroma II, bladder cancer II, and for colon cancer Ib and IIa. Ovarian TAA (gel region 3) and breast TAA (gel region b1-3) are generally separated directly by discontinuous gel electrophoresis.

EXAMPLE 3

Another method used for separating ovarian TAA employs anionic exchange chromatography. An example of this form of separation is as follows. A $0.9 \times 15$ cm column was loaded with washed slurry (0.01 molar $PO_4$ buffer of Bio Rad DEAE 0.6 meq, with 19.2 mg per 4 ml of ovarian cancer cell membrane sonicate separated as follows: Fractions 1 (tubes 1-18) no NaCl, 2 (tubes 19-25) about 0.05M NaCl, 3 (tubes 26-35) about 0.20M NaCl, 4 (tubes 36-39) about 0.25M NaCl, 5 (tubes 40-59) about 0.30M NaCl and 6 (tubes 55-70) about 0.50M NaCl were collected. Total recovery per column was approximately 50% of total protein loaded. Major ovarian TAA bands were present in Fraction 3, but the activity of TAA in producing cell-mediated immunity was much weaker than the product obtained as hereinabove described gel region 3. A more successful use of ion exchange chromatography was possible in isolating Ewing's Sarcoma TAA, as in Example No. 5 hereinafter.

EXAMPLE 4

Recovery of breast TAA both from primary breast tumor and from breast cancer cell line MCF, is shown in Table 3. Electrophoretic mobilities, chemical composition, temperature stability and appropriate molecular weights, as well as a summary of DHR-ST characteristics (see footnotes) are shown in Table 4. Characteristics of breast TAA behavior in double immunodiffusion-immunoelectrophoresis are shown in Table 5. Examples of tests conducted with a particular batch of pure breast TAA (2b1-3) is given in the following Table 6.

TABLE 3

| | Breast Cancer TAA Recovery | |
|---|---|---|
| Washed, viable cells | Primary breast tumor $5 \times 10^9$ (10 gm) | Breast cancer cell line (MCF) $9.69 \times 10^9$ (19.38 gm) |
| Separated membranes: | | |
| soluble protein after sequential sonication | 85 mg | 106.4 mg |
| Fraction II from Sephadex G-200 separation of soluble membrane proteins | 19.24 mg (22.63% of soluble pool) | 29.75 mg (27.9% of soluble pool) |
| Region 2b from PAGE gradient separation of Sephadex fraction II | 1.68 mg (1.97% of soluble pool) | 3.31 mg (3.11% of soluble pool) (2b$_{1-3}$: 2.46 mg; 2a$_1$: 0.85 mg) |
| Soluble protein per cell | 17 picograms | 10.98 picograms |
| Fraction II protein per cell | 3.85 picograms | 3.07 picograms |
| Region 2b protein per cell | 0.34 picograms (2% of soluble protein on the cell) | 0.34 picograms (3.1% of soluble protein on the cell) |
| Region 2a$_1$ (MPV-related) | | 0.09 picograms (0.8% of soluble protein on the cell) |
| Region 2b$_{1-3}$ (TAA) | | 0.25 picograms (2.3% of soluble |

TABLE 3-continued

| | Breast Cancer TAA Recovery | |
|---|---|---|
| Washed, viable cells | Primary breast tumor $5 \times 10^9$ (10 gm) | Breast cancer cell line (MCF) $9.69 \times 10^9$ (19.38 gm) |
| | protein on the cell) | |

TABLE 4

Characteristics of infiltrating ductal breast cancer cell membrane antigens which induce breast-cancer related cell-mediated immune responses.

| Purified antigens | Electrophoretic Mobility (cm distance from tracking dye on gradient PAGE)+ | Chemical composition++ | Stability in pure form* | | | Migration in relation to proteins of known molecular size** |
|---|---|---|---|---|---|---|
| | | | Room temp. 2 hrs. | 4° C. for 2 wk. | −70° C. for 6 mos. | |
| Breast TAA (2b 1–3)[a] | 5.9, 6.2, 6.4 | lipoprotein protein, protein | + | + | + | Gc globulin: migrates 5.1–5.45, 51,000 d |
| | | | | | | Hemopexin: migrates 6.2, 57,000 d |
| | | | | | | Transferin: migrates 6.4–6.5, 76,500 d |
| Breast Tissue Antigen (2a)[b] | 6.8 | glycoprotein | + | ± | ± | |

[a]Elicits a positive DHR-ST in some patients with early stage, but mainly in patients with late stage breast cancer.
[b]Migrates just above breast TAA region; elicits a positive DHR-ST in early (but not late stage) breast cancer patients as well as with patients with other types of gynecologic cancer and is present in some benign breast dyscrasias as well as in the opposite breast in breast cancer patients
+Tracking dye is bromphenol blue (670 daltons); PAGE stacked gels: 3.5, 4.75, 7 and 10%; calculations adjusted for relation of TD to marker albumin in control PAGE.
++Staining individual gels with Coomassie brillant blue, oil red O, periodic acid Schiff.
*As tested by reseparation on SDS-PAGE for intact band and by DHR skin test and LMIT for CMI activity.
**Estimation of precise migration of serum components on control gels; identification of specific components by reactions with monospecific antisera in gel double-diffusion.

TABLE 5

Characteristics of xenogeneic hyperimmune antisera+ to breast tumor-associated antigen*

| Double immunodiffusion tests: | |
|---|---|
| positive with purified breast TAA from: | infiltrating ductal, comedo lobular and medullary breast carcinoma, MCF-7 and HBL-100 breast cancer cell lines and to one fraction (II) of $F_{230}$ cell line. |
| negative to: | cells and fractions I and III of F-230 lymphoid cell line from pleural effusion of breast cancer patient, F-265 lymphocytes of normal donor, H-39 D cell line and fractions, AA-1 bladder cell line, J-82 bladder cell line, T-24 bladder cell line, HCV-29 bladder normal line, HSV-infected WI-38 cells, WI-38 cell, melanoma TAA, nevi, ovarian cancer TAA, normal ovarian tissue, adenocarcinoma lung TAA, colon cancer TAA, fetal black skin, fetal white skin, fetal bladder, fetal liver, fetal intestine, CEA, fibrosarcoma of breast, meningioma cell line, ALL, gastric cancer, hemopexin, alpha-1 acid glycoprotein, transferin, fetal bovine serum, AB-pooled sera. |

+Prepared in albino New Zealand rabbits inoculated monthly × 3 with 28 ug TAA, 4th month bleeding was used, after affinity chromatography procedures, in the above tests.
*Breast TAA: Fairly stable triple polypeptides, approximate mw 55,000d, 57,000d and 75,000d.

TABLE 6

Cell-mediated immunity to PAGE regions 2b 1–3 from an MCF-7 cell line and from infiltrating ductal carcinoma cells tested in cancer patients.

| | | No. positive reactions/total tests (% +) | | |
|---|---|---|---|---|
| Source of extract | Extract PAGE region | Patients with breast cancer | Patients with melanoma | Patients with other types of cancer/ ovarian cancer* |
| Batch 2 MCF-7 breast cancer cells | 2b 1–3 | 11/19 (58) | 0/5 (0) | 0/11 (0) |
| Batch 4 Breast tumor (infiltrating ductal carcinoma) | 2b 1–3 | 28/30 (93) | 0/18 (0) | *0/12 (0) |

ULTRAPURE TAA

The preparation of ultrapure TAA includes the prior steps for the production of pure TAA, and appropriate additional methods to increase the purity of TAA while still maintaining it biologically active and immunogenic. The first of such methods by means of which purity is increased to the ultrapure state is isotachophoresis.

The principle of isotachophoresis is based on migration in an electric field of ion species of the same sign, all having a common counter-ion. The usages have increased since small sample requirements, short analysis time and ease of quantification and accuracy have made it attractive. Isotachophoresis is an electrophoretic separation technique which can be used for both analytical and preparative separations. For analytical separations, I used the LKB 2127 Tachophor, in which the separation takes place in a thermostated capillary tube with no stabilizing medium. The separation of proteins to ultrapure levels is accomplished well by this method in combination with the prior steps.

In preparative isotachophoresis the sample zones migrate with sharp boundaries between a leading and a terminating buffer stacked one behind the other in order of their electrophoretic mobility. The length of each zone is regulated by the amount of sample in the zone. Ampholine spacers, non UV-absorbing, are chosen for mobilities between the sample zones. All the zones then migrate down the column with the same velocity, ensuring that each zone comes off the bottom of the column at the same rate. This means that the peak heights of the eluted zones are independent of the mobility of the different components in the sample. This also means that the last zones coming off the column will have the same resolution and sharpness as the first zones coming off the column. Although this methodology is more difficult as far as the achieving of a good end result than is the analytical method, I did achieve results using the LKB 7900 Uniphor.

The principles of isotachophoresis are well-known. The LKB 2127 Tachophor and LKB 7900 Uniphor are marketed with Instrument Manuals and many Application Notes by LKB Instruments, Inc., Rockville, Md. Other useful articles included, e.g., *Analysis of Complex Protein Mixtures by Capillary Isotachophoresis*, P. Delmotte, *Science Tools*, Vol. 24, pp. 33-41, 1977.

An example of the use of isotachophoresis for the further purification of Ewing's sarcoma TAA is found in the following Example 5.

EXAMPLE 5

Two pathologists made individual assessments of the five materials chosen for study. Two Ewing's sarcoma tissue culture lines (BRL-MR 5838; A4538) were grown until enough wet-packed cells were obtained. Line 5838 was grown to obtain 45.5 grams wet weight of cells. Line A4538 was grown in 80 flasks and 2.4 liters of suspended cells were spun, washed X3 in saline, with incubation before the last wash, and yielded 6 cc of wet-packed cells. Three individual primary tumors yielded single cell suspensions of 4.5 cc, 3.8 cc and 2.7 cc, respectively. Cell membranes were removed by hypertonic to hypotonic stepwise elution methods, as above described, and Lowry protein methods evalutaed an approximate yield of 646.8 mg membrane protein from 5838 preparation, down to 18.4 mg membrane protein from the smallest primary tumor preparation. Evaluation of soluble protein yields after gentle, low frequency sonication, above described, of the separated membrane preparations was more accurate, with yields of 5838 membrane soluble pool protein 222.7 mg, of A4538 protein 58.9 mg, and soluble membrane pools of each of the sonicated membrane preparation of the three primary tumors' cells were 5.55 mg, 4.6 mg and 3.1 mg protein respectively. Evaluation by preliminary discontinuous, gradient polyacrylamide gel electrophoresis indicated that these materials would separate somewhat like our previously studied lymphoma materials, using a series of steps involving Sephadex G-200 to free up the heavier materials. Fractions obtained were tested for HL-A distribution using antisera to markers previously determined on whole cells. In one preparation there was not enough soluble material saved at this step to permit assessment of one of the phenotypes due to the limited availability of strong allo-antisera (if we had saved more, we could have concentrated to get a better reaction). However, all other assessments were done and gave strong confirmation that the HLA markers were present in the heavy molecular weight first peaks off the Sephadex separations. All fractions except the latter were re-pooled for a repeat separation on Sephadex G-125. These fractions were tested for allogeneic lymphocyte migration inhibition using separate ES patient blood samples, and all non-HLA-containing fractions were skin-tested for delayed hypersensitivity reactions in the same patients. Peaks containing reactive material were pooled and separated on Biorad DEAE 0.6 meq, samples concentrated and dialyzed X3 in phosphate buffer, and chloride ions removed; the first separations used aliquots of 5838 soluble membrane G-200-125-derived pool in order to establish a separation pattern. The pattern was drawn and placed on an Ultragrad. The pilot material was tested for reactivity and the cell-mediating immunoreactive samples were identified so that the ultragrad gradient pattern could be established for a constant, controlled method of separation of other samples. Separated fractions were obtained for all five preparations, with aliquots coded and cross-tested in vitro and in non-anergic ES patients and control non-ES age-matched cancer patients. Polypeptide bands of interest were identified in DEAE peaks analytical gel bands. Two were identified as constantly associated with activity. Further purification by isotachophoresis indicated the existence of dimer and monomer forms. Dimer forms (approx. 79,000 d) predominate and constitute approximately 1% of the soluble membrane protein from a single ES cell. ES TAA produced a common cell-mediated immune response and has segments of shared immunity in the two ES cell lines and three ES primary tumors.

Another preparative method in the purification of TAA's is affinity chromatography. Since this method is also used in the preparation of epitopes, methods illustrating a best mode of using affinity chromatography is included in that section.

The next method step that can be utilized to identify and characterize antigenic materials in the production of ultrapure TAA's is the lymphocyte stimulation (LS) assay. Experimental parameters considered in developing LS assays of lymphocyte blastogenic response of immunoreactive lymphocytes to low concentrations of TAA were: (1) Immune status and subpopulations of cells used. (2) Cell viability, concentration, and incubation periods. (3) Synchrony of cell growth phase. (4) Selection of proper controls. (5) Media compositions and (6) Antigen concentration (specific and non-specific).

The general LS procedures used were as follows: Spleen cells and PBLs were isolated by Ficol-hypaque gradient method, washed 2X, resuspended to $2 \times 10^7$ cells/ml in 10% RPMI growth medium. Stimulator cells (used in mixed lymphocyte reaction) were inactivated with 0.25 ug mitomycin C at 30° C. for 30 minutes, washed 3 times and resuspended to $4 \times 10^7$ cells/ml in growth medium. Responder cells at $2 \times 10^7$ cells/ml were untreated. Optimal mitogen concentrations were prepared in growth medium: Phytohemagglutinin (PHA) at 1:160, Pokeweed mitogen (PWM) 1:16. Serial dilutions of TAA were prepared in 10% RPMI. Into 96-well dishes 100 ul of each cell sample at $2 \times 10^6$ cells/ml were plated in triplicate, PHA, PWM, TAA, stimulator cells, or growth medium were added to appropriate wells. Then the cultures were incubated at 37° C. in 7% $CO_2$ for 6 days. Cultures were pulsed early on day 5 with 0.02 uCi/ml of radiolabeled thymidine and harvested late on day 6. Samples were air dried after harvest and counted on day 7 in a scintillation counter.

When all parameters are properly balanced, this is a sensitive and specific test for the assessment of lymphocyte blastogenic response.

The next step in preparing, identifying and characterizing to obtain an ultrapure TAA particularly adapted for the preparation of epitopes therefrom is skin testing for delayed hypersensitive reaction (DHR-ST). A protocol for conducting such skin testing both for pure and ultrapure TAA follows.

Initial skin testing for delayed hypersensitivity reactions is performed, under code, as follows: (1) Prepare a protocol sheet; include age, race, sex, disease, location, degree, stage, current therapy, past therapy, past transfusions and hematologic values. (2) Obtain a signed consent form. (3) Record the code of test materials, inoculate in proper order and cross-check for proper placement when inoculations are completed. (4) Mark the site of each injection with tissue tape (do not cover, and do not wash the injection site). (5) The upper back is more suitable than the arm since the thickness of the skin ensures intradermal administration and the patient appears to have less discomfort; precisely chosen sites equidistant from backbone, inner dorsal area, are used. (6) Tests should be read independently by two investigators who agree closely in readings. (7) Responses are read for immediate reactions and at 24 and 48 hours; in the case of highly purified antigens, they are also read at 72 hours. (8) Induration is the major reaction to be assessed, but the extent of erythema is also recorded. The ball-point pen technique for determining induration boundaries is best. A specific delayed hypersensitive skin reaction is defined as 5 mm induration at 48 hours. (9) Photographs are taken and biopsies of negative and positive reactions are taken for pathologic evaluation. Biopsies of true delayed hypersensitivity skin reactions show 90% mononuclear cell infiltration. (10) For initial tests, we exclude patients from study if they have received chemotherapy or extensive radiation in the previous 14 days; we do not test patients for five, and if practical, ten days or longer after surgery. (11) The test level is kept below 300 mcg protein for membrane preparations and below 100 mcg for pure and below 50 mcg for ultrapure antigens to avoid non-specific reactions. Titrations to 1 nanogram level for reactivity in five patients at each stage are done to determine the minimum dose response.

The next method applied to various antigens to identify and characterize them is enzyme-linked immunoassay (EIA), and preferably one form of EIA: enzyme-linked immunosorbent assay (ELISA).

Enzyme-linked immunoassays (EIA) avoid the hazards and expense of radio immunoassay (RIA) and are equally sensitive. They depend on the use of covalently linked enzyme-antibody complexes in which the complexes are both immunologically and enzymatically active. Detection is by enzymatic activity rather than radioactivity. Horse radish peroxidase and alkaline phosphatase are examples of enzymes that are commonly used for coupling for antibodies. They can convert colorless substrates to colored products which, under defined conditions, can be measured. One appropriate EIA for measuring candidate biologic markers in human serum is believed to be enzyme-linked immunosorbent assay (ELISA). Two different antibodies bind to the candidate biologic marker (CBM). The first antibody of the system, which is specific for the CBM, is absorbed to a solid matrix. The second antibody, which has been generated in a different species, also binds CBM. The antibody of the enzyme-antibody complex binds to the second antibody of the system and the enzyme converts the substrate to products. A variation of this procedure is the sandwich type ELISA. Examples of the use of EIA and ELISA for characterizing TAAs and antibodies therefrom are found hereinafter, e.g., example 7.

An example of the separation, identification and characterization of lung TAA in pure and ultrapure form is summarized by a flow diagram identified in Example 6 and by Tables 7 to 10 of pertinent studies in preparation for pilot clinical analyses as follows.

EXAMPLE 6

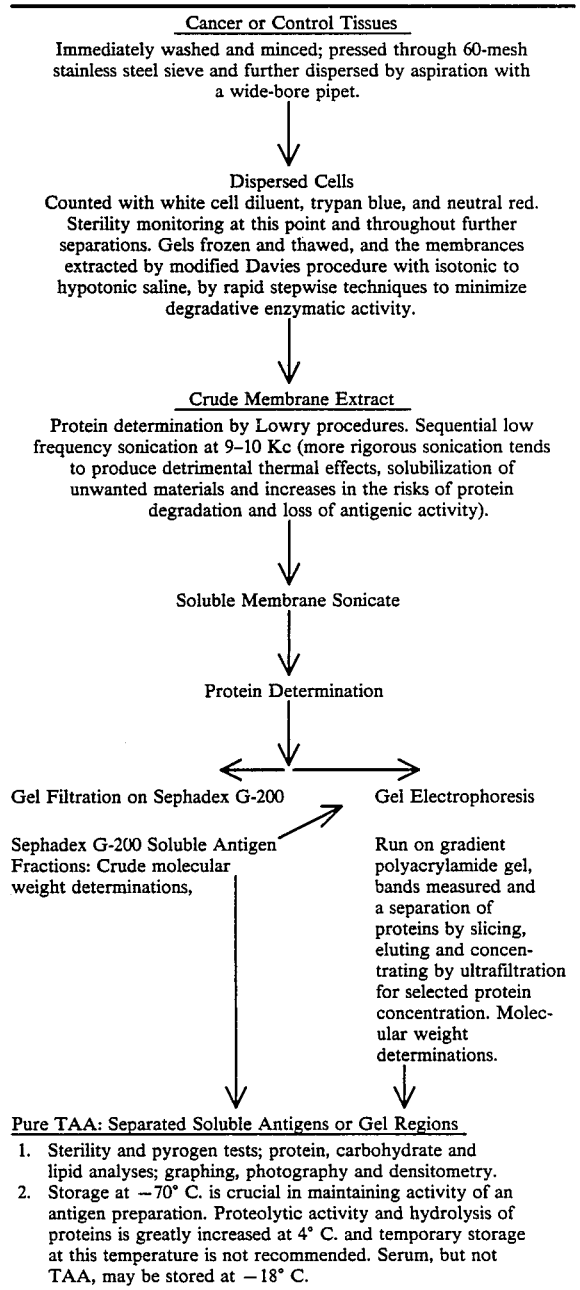

FLOW DIAGRAM OF LUNG TAA SEPARATION

Cancer or Control Tissues
Immediately washed and minced; pressed through 60-mesh stainless steel sieve and further dispersed by aspiration with a wide-bore pipet.

Dispersed Cells
Counted with white cell diluent, trypan blue, and neutral red. Sterility monitoring at this point and throughout further separations. Gels frozen and thawed, and the membrances extracted by modified Davies procedure with isotonic to hypotonic saline, by rapid stepwise techniques to minimize degradative enzymatic activity.

Crude Membrane Extract
Protein determination by Lowry procedures. Sequential low frequency sonication at 9–10 Kc (more rigorous sonication tends to produce detrimental thermal effects, solubilization of unwanted materials and increases in the risks of protein degradation and loss of antigenic activity).

Soluble Membrane Sonicate

Protein Determination

Gel Filtration on Sephadex G-200

Sephadex G-200 Soluble Antigen Fractions: Crude molecular weight determinations, Gel Electrophoresis Run on gradient polyacrylamide gel, bands measured and a separation of proteins by slicing, eluting and concentrating by ultrafiltration for selected protein concentration. Molecular weight determinations.

Pure TAA: Separated Soluble Antigens or Gel Regions
1. Sterility and pyrogen tests; protein, carbohydrate and lipid analyses; graphing, photography and densitometry.
2. Storage at −70° C. is crucial in maintaining activity of an antigen preparation. Proteolytic activity and hydrolysis of proteins is greatly increased at 4° C. and temporary storage at this temperature is not recommended. Serum, but not TAA, may be stored at −18° C.

FLOW DIAGRAM OF LUNG TAA SEPARATION (continued)

3. Skin test material.
4. In vitro assays.

↓

Ultrapure TAA

5. Separation by isotachophoresis and/or monoclonal antibody affinity chromatography.
6. Monoclonal antibodies for ELISA and for isotope tagging for use in testing localization in tumors.
7. N-terminal and primary amino acid sequencing.
8. Use in preparation of monoclonal antibody-derived epitopes.

↓

TAA Epitopes

1. Measurement of specific and non-specific antibody responses.
2. Identification and characterization of epitopes from primary and metastatic TAA for presence of epitopes and for identification of changes, modulations, and alterations as well as similarities.
3. Testing of selected epitopes with a battery of sera from patients undergoing therapy.
4. Utilization of TAA monoclonal antibodies and monoclonal antibody-derived epitopes in preparation of a cascade of idiotype, anti-idiotype, anti-anti, anti-anti-anti, etc.
5. Studies of epitope and combinations with one or more epitopes for effectiveness in including cell-mediated immune responses in vitro and in vivo.

TABLE 7
SKIN TESTS OF ENTIRE SPECTRUM OF FURTHER SEPARATED LUNG CELL SOLUBLE MEMBRANE ANTIGENS

Normal lungs grouped for further DHR-ST studies

| Approximate Age | Number in Pool |
|---|---|
| Group 1 Fetal 7 to 8 weeks | 3 sources |
|  | 5 specimens |
| Group 2 Fetal 14 to 14 ½ weeks | 5 sources |
|  | 6 specimens |
| Group 3 Fetal 16 weeks | 3 sources |
|  | 7 specimens |
| Group 4 Fetal 20 weeks | 2 sources |
| Group 5 Adult traffic accident victim, 17 years | 1 source |

TESTS AND CONCLUSIONS

Testing of 19 lung cancer patients with membranes, soluble pools, Sephadex fractions; CMI+ reactions were seen to Sephadex fractions of Groups 1, 4 and 5; gel patterns, densitometry, testing in 4 lung cancer and 4 non-lung cancer patients of separated, eluted and concentrated band regions of all groups; 4 positive regions identified: 3 in Group 1, 1 in Groups 4 & 5; further purification for Groups 1, 4 and 5 of each reactive band region; retesting, characterization and analysis over a period of months; titrations in preparation for cross-testing study.

TABLE 8
TESTS OF COMMON CMI-PRODUCING TAA DHR-ST CROSS-TESTING OF: SEPARATED POLYPEPTIDE BANDS

| Group 1 | Early fetal | 3 antigens |
|---|---|---|
| Group 4 and 5 | Late fetal | 1 antigen |
| Group 6 | Squamous cell carcinoma | 5 antigens |
| Group 7 | Adenocarcinoma | 4 antigens |
| Group 8 | Oat cell caroinoma | 4 antigens |
| TOTAL | | 17 antigens |

**FOR TESTING IN PATIENTS* WITH:**

A. Squamous cell lung cancer
B. Adenocarcinoma lung
C. Oat cell lung cancer
D. Non-lung cancers

*10-15 patients of each type were each tested ID on back with each of 17 antigens; over 5 mm I reactions were considered positive; cross-reactive antigens were seen for two antigens of Groups 1, 6 & 7 (fetal, squamous cell and adeno) and two antigens of Groups 7 & 8 (adeno and oat); one of the Group 8 antigens did not test as consistently positive in C patients and was not a candidate.

TABLE 9
TESTS OF COMMON CMI-PRODUCING TAA (Cont.)
Number of Patients* with Positive DHR-ST.**

| Antigens Tested: | A(15) Epid | B(15) (Adeno) | C(10) (Oat) | D(12) (non-lun) |
|---|---|---|---|---|
| Group 1+: | | | | |
| fetal ag++1 | 13 | 0 | 0 | 1 |
| fetal ag 3 | 15 | 12 | 0 | 3 |
| fetal ag 4 | 15 | 15 | 0 | 1 |
| Group 4 & 5: | | | | |
| fetal ag 2$ | 10 | 0 | 0 | 1 |
| Group 6: | | | | |
| epid. ag 1φ | 14 | 2 | 0 | 1 |
| epid. ag 2$ | 14 | 4 | 0 | 1 |
| epid. ag 3 | 13 | 14 | 1 | 1 |
| epid. ag 4 | 15 | 12 | 0 | 1 |
| epid. HSV-TAA | 15 | 6 | 0 | 4 |
| Group 7: | | | | |
| adeno. ag 1§ | 1 | 15 | 10 | 3 |
| adeno. ag 2§§ | 0 | 15 | 9 | 0 |
| adeno. ag 3 | 12 | 14 | 1 | 3 |
| adeno. ag 4 | 11 | 12 | 0 | 1 |
| Group 8: | | | | |
| oat ag 1§ | 2 | 11 | 10 | 1 |
| oat ag 2§§ | 3 | 10 | 0 | 1 |
| oat ag 3 | 1 | 0 | 8 | 1 |
| oat ag 4 | 2 | 0 | 3 | 1 |

+See Table 2.
++SDS banded material with same 3 terminal amino acids
*Attrition: 2 anergic, 1 discharged early before could read tests and 1 quit after 4th injection (4/56 = 7%).
**If number positive are greater than 2/3rds of patients tested in that category, then antigen is probably allogeneic; only one selected protein concentration was tested in these series.
φFetal ag 1 is also present in epid. (ag 1 of group 6).
$Fetal ag 2 is also present in epid. (ag 2 of group 6).
Fetal ag 3 is also present in epid. (ag 3 of group 6) and adeno. (ag 3 of group 7).
Fetal ag 4 is also present in epid. (ag 4 of group 6) and adeno. (ag 4 of group 7).
§This antigen is shared by adeno. (ag 1 of group 7) and oat cell (ag 1 of group 8).
§§This antigen is shared by adeno. (ag 2 of group 7) and oat cell (ag 2 of group 8).

TABLE 10
CHARACTERISTICS OF LUNG CELL MEMBRANE ANTIGENS WHICH INDUCE CELL-MEDIATED IMMUNE RESPONSES

| | Electrophoretic Mobility (cm distance from tracking dye on PAGE)* | Chemical Composition** | Stability in pure form | | | Migration in relation to control proteins of known molecular size |
|---|---|---|---|---|---|---|
| | | | Room Temp 2 hrs | °C. for 1 week | −70° C. for 6 mo. | |
| Squamous Cell Cancer: | | | | | | |
| Fetal Ag 1 | 5.3 | protein | + | + | + | Gc globulin: migrates 5.1–5.45 51,000d |
| Fetal Ag 2 | 8.4 | lipo-protein | + | + | ± | Haptoglobin type 1: migrates 8.4 100,000d |

TABLE 10-continued

CHARACTERISTICS OF LUNG CELL MEMBRANE ANTIGENS WHICH INDUCE CELL-MEDIATED IMMUNE RESPONSES

| | Electrophoretic Mobility (cm distance from tracking dye on PAGE)* | Chemical Composition** | Stability in pure form | | | Migration in relation to control proteins of known molecular size |
|---|---|---|---|---|---|---|
| | | | Room Temp 2 hrs | °C. for 1 week | −70° C. for 6 mo. | |
| Fetal Ag 3 | 9.2 | protein | + | + | + | Haptoglobin type 2.2: migrates 8.9 400,000d |
| Fetal Ag 4 | 10.2 | protein | + | + | ± | β-lipoprotein products: migrates 9.6–9.95, unknown |
| HSV-TAA | 3.25, 3.85 | protein | + | ± | + | Thyroxin-binding prealbumin: migrates 3.4, 61,000d α-1-acid-glycoprotein: migrates 4.0, 40,000d |
| Adenocarinoma: | | | | | | |
| Fetal Ag 3 | 9.2 | protein | + | + | + | see above |
| Fetal Ag 4 | 10.2 | protein | + | + | + | see above |
| TAA 1 | 5.4 | protein | + | + | + | Gc globulin: migrates 5.1–5.45 51,000d |
| TAA 2 | 7.3 | protein | + | + | + | Hemopexin: migrates 6.2 57,000d Transferin: migrates 6.4–6.5 76,500d |
| Oat Cell: | | | | | | |
| TAA 1 | 5.4 | protein | + | + | + | see above |
| TAA 2 | 7.3 | protein | + | + | + | see above |
| TAA 3 | 6.6 | lipo-protein | + | + | ± | Transferin: migrates 6.4–6.6 76,500d |
| Fetal Lung (7–8 weeks): | | | | | | |
| Ag 1 | 5.3 | protein | + | + | + | see above |
| Ag 3 | 9.2 | protein | + | + | + | see above |
| Ag 4 | 10.2 | protein | + | + | ± | see above |
| Adult Normal Lung: § | | | | | | |
| Ag 2 | 8.4 | lipo-protein | + | + | ± | see above |

*Tracking dye is bromphenol blue (670 daltons): PAGE stacked gels: 3.5, 4.75, 7.0 & 10%: calculations adjusted for relations of TD to marker albumin in control PAGE.
**Staining individual gels with Coomassie brilliant blue, oil red O, periodic acid-Schiff.
As tested by reseparation on PAGE for intact band and by DHR-ST and LMIT for CMI activity.
§Also present by 20 weeks in fetal lung.
Estimation of precise migration of serum components on control gels; identification of specific components by reactions with monospecific antisera in gel double-diffusion.

To establish further the specificity of a lung TAA, a patient with adenocarcinoma of the lung received approximately 200 uCi of In[111] covalently bound to the affinity-purified human IgG antibody to purified TAA. Chest scans showed localization in the sites of known loculated malignant pleural effusions.

TAA EPITOPES

BACKGROUND OF THE INVENTION

The classical description of an epitope is that it is a defined antigenic determinant. Described for the first time in this application is the isolation of a particular piece or part of a TAA polypeptide which produces a defined reactivity. Thus, TAA epitopes are defined antigenic determinants of a certain specificity if they are represented by the same macroantigen (TAA). According to my invention, TAA epitopes are obtained from the larger polypeptide TAA by using standard techniques for the preparation of monoclonal antibodies (Mab) to TAA, then using affinity chromatography for the separation of antibody-antigen complexes, pH manipulation of the complex to separate the antigenic determinat (epitope) from the antibody, and the analysis of their activities in enzyme immunoassays. To my knowledge, no epitopes have been derived from TAAs of demonstrated clinical application in immunotherapy. To my knowledge, no epitopes have ever before been shown to be useful as monitors of specific active immunotherapy. To my knowledge, this is the first usage of TAA epitopes for measuring specific antibody responses in patients undergoing immunotherapy.

Not only has there been no immunoassay which specifically follows and monitors the course of events in the patient during the early period after immunotherapy with biologic drug TAA, but also it has heretofore not been possible to characterize an epitope of TAA which is suitable for monitoring the presence of TAA antibodies in the blood of patients having cancer with a monitoring test suitable for predicting the efficacy of TAA immunotherapy early after administrating said immunotherapy.

The inventor herein describes the detailed methods and procedures followed in development and identification of said epitopes, the method of utilizing these epitopes in a monitoring test, the application of these tests to clinical testing, and some of the results therefrom. The approach has been expanded to include many cancer TAA epitopes, and current reports of epitopes so identified and established as useful for critical analyses of cancer progression as well as for monitoring tests include melanoma, colon, larynx, lung and other types of cancers.

SUMMARY OF INVENTION

The present invention basically describes the making of an epitope from a tumor-associated antigen (TAA), which TAA is capable of generating a specific immunotherapeutic response. In a broad form, the method comprises injecting the TAA into a host animal to stimulate the production by lymphocytes of antibodies specific to the TAA; fusing the lymphocytes with an immortal cell line to form hybridomas capable of secreting selected monoclonal antibodies reactive with the TAA; dividing the TAA into fragments including epitopes with antigenic and immunogenic properties, having specific reactivity with the monoclonal antibodies, and forming complexes between the epitopes and the monoclonal antibodies. These complexes are then separated, and the TAA epitopes recovered.

The TAA epitopes may be identified and characterized by a variety of methods and in combinations thereof, e.g., by measuring specific and non-specific antibody responses to the epitopes; by measuring changes, modulations, alterations and similarities with primary and metastatic TAA; by testing the epitopes with a battery of sera from patients undergoing therapy; by utilizing the epitopes and monoclonal antibodies in the preparation of a cascade of idiotype, anti-idiotype, anti-anti, anti-anti-anti, etc., and by measuring the effectiveness of the epitopes in inducing cell-mediated immune responses in vitro and in vivo.

In another aspect, the invention is directed to a method of making an epitope in which as stated hereinbefore, TAA is injected into a host animal and the lymphocytes produced thereby are fused with an immortal cell line to form hybridomas capable of secreting selected monoclonal antibodies reactive with the TAA. Such Mabs are then coated onto beads for affinity chromatography to form monoclonal antibody-conjugated beads. TAAs are added to the beads to form TAA-Mab complexes thereon, which are insoluble in a neutral, aqueous medium. Then the complexes are dissociated to recover the TAAs, which are thereafter divided into fragments including epitopes having specific reactivity with the Mabs. Thereafter the TAA fragments are added to the Mab-conjugated beads to form epitope-Mab complexes, which are later separated to recover TAA epitopes capable of reacting with Mabs having the ability to bind to the TAA.

As has been stated, the starting material for the preparation of epitopes of tumor associated antigens is preferably an ultrapure TAA as defined in and produced by the practice of the aforesaid methods. Beginning with such ultrapure TAA in the preferred embodiment of my invention, the first step is to produce a hybridoma cell line from the antigen.

Protocols for the construction of antibody producing hybridomas were based upon state-of-the-art procedures. Procedures were also used to conduct preliminary screen tests for hybridoma selection by EIA to a battery of normal, benign and cancer cell-derived, soluble membrane separated proteins and TAAs in order to rule out or in cross-reactions. A secondary screen was to a battery of selected primary and metastatic TAAs of the related cancer. Standard procedures were used to grow up enough cloned cells for production of Mabs for EIAs and for use in affinity chromatography.

Rather than insert here the entire protocol for the production of antibody-producing hybridomas, it can be stated that the techniques followed were based upon the Kohler-Milstein discovery. These techniques will be apparent from the following references:

Kohler, H. and Milstein, C. (1975) "Continuous cultures of fused cells secreting antibody of predefined specificity." *Nature* 256: 495-497. Kennett, R. H., McKearn, T. J. and Bechtol, K. B. (1980) *Monoclonal Antibodies. Hybridomas: A New Dimension in Biological Analyses* Plenum Press, New York. Langone, J. J. and Van Vunakis, H. (1983) Immunochemical Techniques. Part E. Monoclonal Antibodies and General Immunoassay Methods. *Methods in Enzymology* v. 92. Academic Press, New York pp. 1-647.

After the procedures for the formation of monoclonal antibodies had been performed, candidate monoclonal antibodies were tested in enzyme immunoassays for activities and selected for use in affinity chromatography procedures as follows: Mab is dialyzed with 0.01M $PO_4$ buffer pH 7.4. 0.5 gm CNBr Sepharose is dissolved in 200 ml $10^{-3}$M HCl; then washed on a glass filter with 200 ml of $10^{-3}$M HCl and transferred to a tube, allowed to settle and buffer is removed. This is combined with Mab and mixed end over end overnight at 4° C. The mixture settles, the supernatant is removed and mixture is washed with several volumes of the coupling buffer (0.1M $NaHCO_3$/0.5M NaCl). A Lowry is performed on the supernatant to determine protein concentration. The buffer is removed and reacted with 5 ml of 1M ethanolamine at pH8 for 2 hours. The ethanolamine is removed and mixture is washed with coupling buffer. It is then washed with acetate buffer (0.1M $CH_3COO$/1.0M NaCl) at pH4.0 and, afterward, is washed with borate buffer (0.1M $BO_3$/1.0M NaCl) at pH8.0. These two washings are repeated in sequence twice more. The beads are washed three times in 0.01M $PO_4$ buffer at pH 7.4 and resuspended in the same solution. They are packed in a 0.7×10 cm column at 4° C. TAA is loaded in 1.5 ml amount and reacted for 90 minutes. It is then washed with loading buffer until O.D. at 280 nm falls off, collecting 1 ml fractions (TAA is prepared by dialyzing purified antigen in 0.1M $NaHCO_3$/0.5M NaCl buffer to a final concentration of 10 mg/50 ml). Elutions are with 10 ml 0.55M NaCl in 0.01M $PO_4$ buffer, and 1 ml fractions are collected. Then bound material is eluted with 10 ml Sorensen's glycine I at pH 2.8, 1 ml fractions are collected and neutralized with 1M Tris. Then a subsequent elution with 10 ml 0.01M $PO_4$ at pH 7.4 is carried out and 1 ml fractions collected. The neutralized fractions are collected and dialyzed in 0.1M $PO_4$. Depending on the nature of the complexes formed by different antigens with the insoluble Mab, different antigens will be eluted at different salt concentrations. Standard enzymatic separation is an alternative method. The eluate is then neutralized before testing in enzyme immunoassays. Following degradation, fractionation or fragmentation of the eluted material, the derived fragments can be recycled.

An example to illustrate the method and application is given an Example 7.

EXAMPLE 7

Lung cancer TAA epitopes: Epitopes were used for the evaluation of lung cancer patients in specific active immunotherapy trials to measure various immune responses both prospectively and retrospectively. These studies are useful for the design of future trials, which may involve the combination of TAA specific active immunotherapy with other promising therapeutic agents, including drug therapy and biologic drug therapy. One of these monitoring techniques, a serial monitoring test, has permitted monitoring the patient's early response to immunotherapy and to predict early in the course of the trial whether or not that patient has responded to immunization. Certain monoclonal antibody-derived epitopes were more sensitive and selective for detection of antibodies in patient sera than were monoclonal antibodies alone used in competitive indirect enzyme immunoassays. Some of the lung tumor TAA epitopes are non-specific, while others appear to be quite specific with regard to well-defined primary lung tumor histopathology subtypes.

Shown in FIG. 1 is an example of enzyme assays performed to epitope D36h6. In this study, monoclonal antibodies were prepared to a lung squamous cell TAA which in purified form is 37,000 daltons. As illustrated, D36h6 was the least cross-reactive of the monoclonal antibody purgation derived epitopes prepared from the 37Kd TAA. Only 5% of non-lung cancer and non-squamous cell cancer sera reacted in the assay, and then only at upper concentrations greater than 60 nanograms which was outside the limits of test sensitivity. There were no cross-reactivities seen to normal sera. Thus, any control sera responses were at the limits of the reaction and did not compare to levels of sensitivity seen in sera from patients at indicated time periods after receiving squamous TAA specific active immunotherapy. All sera were from non-anergic, untreated patients and from age-sex matched controls. In one set of immunoassay studies, dilutions of the epitopes, ten-fold, 60 to 10 nanograms, were tested in triplicate against 5 (first, second, third monthly immunization periods, at 5-6 months and at 9-12 months) serial sera from each of 22 patients who had received immunotherapy, and from each of 20 matched patient controls. This was a total of 3,780 enzyme-linked immunosorbent assays. As shown, there is a burst of antibody to the epitope at or shortly after the second immunization. This level increases at the third immunization and remains or keeps rising for another 2 or 3 months and then subsides to the tissues. In contrast, in separate studies of patients with lung cancer stage 3, who failed therapy, there was no rise in antibody response seen at the time of the first and second immunization. One patient showed a positive response at the weakest limit at the third immunization, and all patients who failed therapy also failed to sustain antibody responses, as measured by negative responses at 5-6 months. This particular type of monitoring permits one to measure specific responses to TAA immunization, and is useful and sensitive enough for early monitoring so as to provide prognostic signals as to the efficacy and/or futility for continuing specific active immunotherapy. With this capability to monitor early antibody rises in the blood stream, we also have a way to follow the response to specific active immunotherapy singly or when combined (and can thus measure the effect upon) with another form of immunotherapy or chemotherapy.

Examples of the preparation of pure and ultrapure colon TAA, identification and characterization thereof, and the preparation of TAA epitopes therefrom are set forth in detail in the next examples for colon cancer (example 8), melanoma (example 9) and laryngeal cancer (example 10).

EXAMPLE 8

In one separation procedure, 56 colon tumors from hepatitis-free donors were processed by procedures hereinabove described to obtain cells, membranes, and solubilized proteins from the separated membranes. As described, soluble proteins were then separated using Sephadex G-200, and the final yield of pure TAA fraction (IB+IIA) was 108.5 mg protein. Individual bands were separated by above described gel electrophoresis methods and used for identification and characterization of active components. Two bands were identified as producing cell-mediated reactivity. Approximate molecular weight in SDS discontinuous gel electrophoresis was calculated for band a as 72,000d and band b as 88,000d. Each band was biologically active as measured by delayed hypersensitivity skin tests and specific lymphocyte stimulation by above described methods. The stability in pure form at room temperature for two hours was +, for 4° C. for 1 week was ±, and at −70° C. for two years was +. It was further established that colon TAA in pure form was free of any detectable serum components, from inhibitory or interfering factors, and from DNA and from HLA major components. TAA constituted 2 to 3% of separated, soluble cell membrane protein.

In an assessment of individual tumor soluble pools, it was seen that TAA is weakly present in some tumors and strongly present in others. TAAs from primary tumors cross-reacted in double immunoelectrophoresis-immunodiffusion and in enzyme-linked immunosorbent assays. The more sensitive enzyme immunoassays had to be performed to selected TAA epitope CTAA 68d4 as this particular assay is quite selective. For this and other purposes, monoclonal antibodies were prepared to ultrapure TAA band a as further purified by isotachophoresis hereinabove described. Band a was chosen for first studies, since other separations of metastatic tumors (where colon tumor was the primary) showed that some of these tumors have altered or non-existent primary TAA band b and a new or structurally-altered band sometimes induces cell mediated immune responses and may be identified between 85000d and 89000d. Cross-testing of over 200 non-colon cancer and normal tissue preparations and serum components by double immunodiffusion-immunoelectrophoresis demonstrated colon tumor cell membrane specificities for colon TAA at that level of sensitivity. More sensitive cross-testing by enzyme-linked immunosorbent assay was performed to selected TAA epitope 68d4 and other monoclonal antibody-derived antigenic determinants; these tests indicated a high degree of tumor-related specificity for certain epitopes, namely 68d4 and 68d1, but not for others studied at this time, suggesting shared immunologic identity for portions only of the TAA amino acid chains.

The yield of TAA from appropriately characterized colon tumor cells is approximately as follows: TAA a, b make up about 0.3 picograms per cell. It takes approximately $10^9$ cells to yield 300 micrograms. Other immunoreactivities tested by above described methods showed that pure colon TAA utilized at low concentrations stimulates a dose-dependent, sensitive and selective lymphocyte blastogenic response in antigen-primed human splenocytes. Dose-related immunoreactivities, as measured by delayed cutaneous hypersensitivity skin tests and by migration inhibition assays showed that patients develop a strong postimmunization response approximately five to six months postimmunotherapy. TAA immunizations induced strong delayed hypersensitivity reactions which were highly specific and both autologous and allogeneic TAA, derived from separated soluble colon tumor membrane preparations, induced titrated nanogram to picogram reactivity up to nine years or longer post-immunization, indicating a long, specific immunologic memory in patients responding to colon TAA specific active immunotherapy.

No autoimmune reactions after TAA immunotherapy have been observed; specifically, patients had no enteritis, indicating that preparations are free from major normal HLA antigens, which might induce any autoimmune reactivities. Sensitive tests of TAA using 3T3 cell cultures, ethidium bromide assays, HTLVIII electroblot antibody and antigen receptor tests, a battery of indirect chromium release assays and hepatitis antigen kit tests as well as previous tests for hepatitis of sera from all tumor donors have established that TAA preparatories do not cause cell transformation contain less than 10 picograms DNA, are free of AIDS viral components, are free of major HLA and of hepatitis viral components, respectively. As above described, primary colon TAAs share certain immunologic identity, but metastatic colon TAAs sometimes are altered or modulated.

Figure 2:
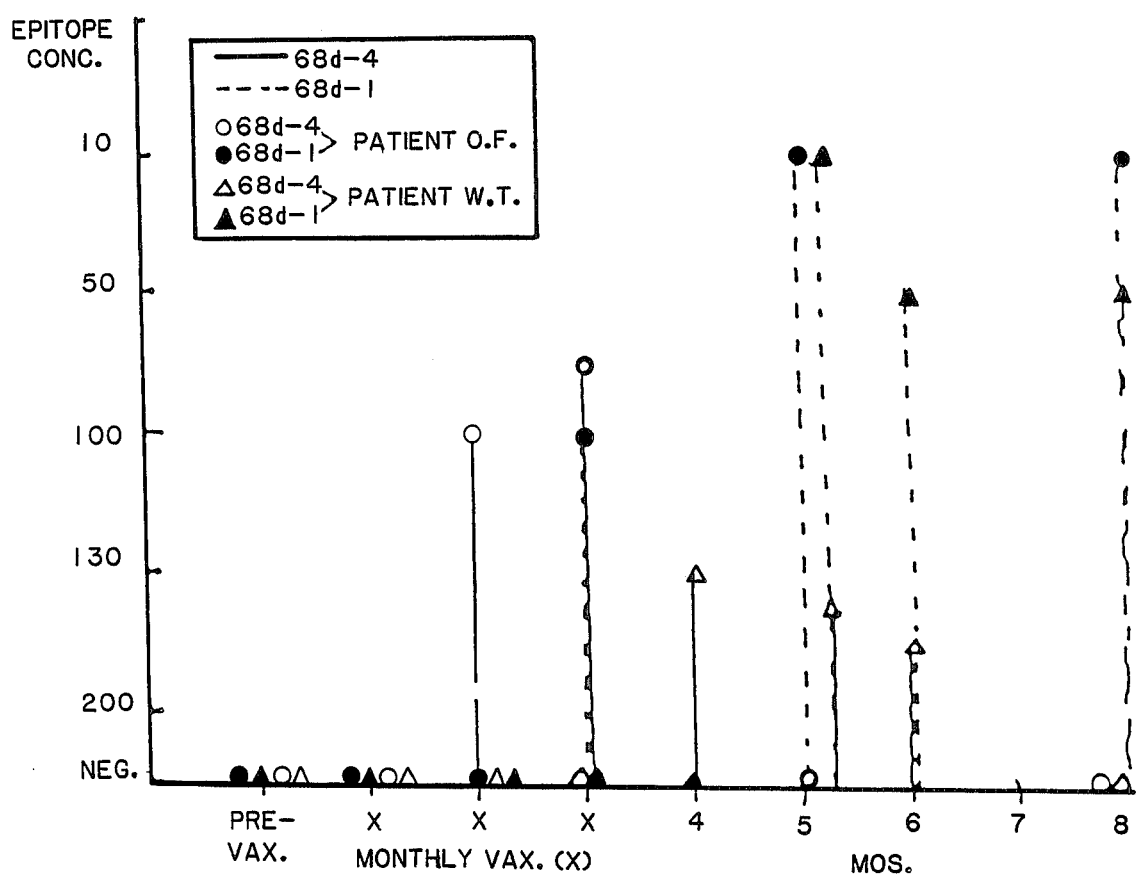

Observations using enzyme-linked immunosorbent assays of an array of twelve candidates, based upon reactivity with control, hyperimmune and immunized patient sera permitted the sorting out of two selected epitopes which appeared to be more specific: no cross-reactivity with age- and sex-matched normal sera (0/30), less than 6% cross-reactivity with sera from non-immunized (1/28) and immunized (2/30) lung cancer patients, and, with greater than 80% reactivity with immunized colon cancer patient sera at the time of receiving a third vaccine (15/18). These two epitopes were quite different in reactivity when tested against serial sera from patients undergoing immunotherapy. Epitope 68d-4 appears to measure earlier TAA antibody levels in patients on immunotherapy, as in contrast to epitope 68d-1 which appears to measure somewhat later responses, although still early. This may indicate that there is at least a post-immunization bi-level antibody response, which is illustrated in FIG. 2.

Shown are examples of assays of serial sera from two patients using the two epitopes. Titrations were run in triplicate and levels of responses to epitopes 68d-1 and 68d-4 were compared before, during and up to eight months after immunotherapy. The examples in FIG. 2 are: patient O.F. who had no recurrence and patient W.T. who had recurrence of cancer. Patient O.F. is a 64 year old female with stage Duke's C, with three out of 10 positive lymph nodes. At eighteen months this patient is disease-free and alive. Patient W.T. is a 58 year old male with stage Duke's C with 3 out of 6 positive lymph nodes. His disease-free survival was 11 months and this patient is still alive at 18 months. When these data were compared with assessments of immune complexes performed with blood specimens taken at the same time intervals, it was of interest to note that while patient O.F. had normal profiles, patient W.T. gave classical indications of impending immune shutdown by 8 months post-therapy. In LS tests, above-described, epitope 68d-4 was recognized by peripheral blood lymphocytes from patient O.F. at the time of her third vaccination but not be control normal lymphocytes, indicating that the epitope is a distinct antigenic determinant.

LEGEND FOR FIG. 2

Colon cancer TAA epitopes 68d-1 and 68d-4 dilutions were tested in triplicate versus sera from patients O.F. and W.T. at pre-vaccination, and the three monthly immunization periods, at 5 months and 8 months, with additional sera tested from patient W.T. at 4 and 6 mos. The enzyme immunoassays, standarized with reactivity to monoclonal antibody, and controlled with other sera of known reactivity, were repeatable in all three tests with each of the epitopes (a total of 540 assays). As shown, epitope 68d-4 appears to measure earlier TAA antibody levels induced in patients on immunotherapy, as in contrast to epitope 68d-1 which appears to measure somewhat later responses, although still early. The patients were well-matched for stage (Duke's C, three positive nodes) and age (64 yr, 58 y), but at 18 mos. O.F. is disease free and W.T. is alive, but with a history of recurrence at 11 mos., which may be indicated by the later, lower-titer response to epitope 68d-4. Epitope 68d-1 is less well studied at this time.

EXAMPLE 9

The above methods have been used to carry out the formation, identification and characterization of melanoma TAA and epitopes. The results of such preparation and characterization of melanoma TAA and epitopes are recited hereinafter in Table 11, where the epitopes 63a12, 69b8 and 14g2 were obtained.

TABLE 11

Melanoma Tumor-Associated, Oncofetal and Tissue-Associated Antigens, Monoclonal Antibodies and Epitopes I Melanoma tumor- and tissue-associated antigens

| | chemical composition | molecular weight | stability in pure form |
|---|---|---|---|
| Melanoma TAA- | glycolipoprotein | complex form | 4° C.: 3 days +; 1 week |
| | | | −70° C.: one year + |
| | lipoprotein active component | 216,500 d | 4° C.: 1 week +; 2 weeks |
| | | | −70° C.: one year + |
| Fetal antigen #1 | protein | 54,700 | 4° C.: 1 week +; |
| Fetal antigen #2 | protein | 52,500 | −70° C.: one year + |
| Tissue associated antigen #1 | lipoprotein | 46,000 | 4° C.: 1 week + |
| | | | −70° C.: one year + |
| Tissue associated antigen #2 | lipoprotein | 44,000 | |
| Fetal antigen #3 | protein | 32,000 | 4° C.: 1 week +; |
| | | | −70° C.: one year + |

II Cell-mediated immunoreactivities to melanoma tumor- and tissue-associated antigens:

Melanoma TAA- elicits a positive DHR-ST in 88% patients with early stage systemic and ocular melanoma, in 37% patients with advanced systemic melanoma, and with approx. 3% positivity seen in patients with other cancers.

Pooled Melanoma tissue-associated antigens (includes fetal antigens) - more broadly reactive, giving positive reactions in 43% patients with early stage systemic melanoma; strongly in 72% patients with advanced stages of melanoma; also produce some positive responses in patients with

TABLE 11-continued

Melanoma Tumor-Associated, Oncofetal and Tissue-Associated Antigens, Monoclonal Antibodies and Epitopes other malignancies but mainly in patients with breast cancer III Reactivities of hyperimmune xenogeneic antisera and monoclonal antibodies to melanoma tumor- and tissue-associated antigens:

A. Double immunodiffusion-immunoelectrophoresis with TAA xenogeneic antisera and hyperimmune patient monospecific antisera:
Positive to purified melanoma TAA from 73 primary melanoma tumors (three were amelanotic) and 8 of 9 melanoma liver metastases.
Negative to extracts of fetal black skin, fetal white skin, fetal intestine, normal lung tissue from a melanoma patient, $MCF_7$ breast cancer cell line, whole and fractionated AB pooled sera, 18 breast cancer tumor extracts, 15 lung cancer extracts, 8 colon cancer extracts, two bladder cancer cell lines, angioma, HSV-infected WI-38 cells, WI-38 cells, 42 nevi extracts, ovarian cancer TAA, normal ovarian tissue, white skin, black skin, adenocarcinoma lung TAA, colon cancer TAA, fibrosarcoma of breast, meningioma cell line, ALL cells, gastric cancer tumor extracts, hemopexin, normal white blood cells, alpha 1-acid glycoprotein, transferin.

B. Indirect immunofluorescence tests for presence of TAA in wet tumor tissue imprints:
Xenogeneic TAA antisera for melanoma and two control sera (squamous cell TAA antisera and ABO pooled normal sera) were tested in triplicate with wet tumor imprints.
Positive reactions in 16 wet tumor tissue imprints from melanoma patients as well as to one melanoma TAA-containing cell line (Gi).
Negative reactions to 3 wet tumor tissue imprints from melanoma patients as well as to fresh wet tumor tissue imprints from 7 breast tumors and 8 lung cancer specimens.

C. Enzyme immunoassays (ELISA) with melanoma TAA monoclonal antibodies M460e and M503a:
M460e Mab positive: 18 of 21 melanoma, 2 of 16 breast cancer and 0 of 12 lung cancer specimens
M503a Mab positive: 14 of 21 melanoma (2 were different tumors of the same group tested with M460e as negative to the latter Mab), 0 of 16 breast cancer and 0 of 12 lung cancer specimens D. ELISA with melanoma TAA Mab M460e- and M503a- derived epitopes:
M460e-derived epitope 63a12: 106 of 211 sera from hyperimmune melanoma patients on immunotherapy were positive. 0 of 31 sera from lung cancer patients also on (lung TAA) immunotherapy were positive. 0 of 26 sera from breast cancer patients were positive.
M460e-derived epitope 69b8: only 5 of 211 sera from melanoma patients and 3 of 26 sera from breast cancer patients were positive; 0 of 31 sera from lung cancer patients were positive.
M503a-derived epitope 14g2: 206 of 211 sera from melanoma patients and 0 of 26 sera from breast cancer patients and 0 of 31 sera from lung cancer patients were positive.

E. Double immunodiffusion-immunoelectrophoresis with nonspecific tissue and fetal pooled antigens:
Fetal antigens #1, #2, #3: cross-reacted with separated fetal black skin antigens and with 2 of 42 nevi extracts.
Fetal antigen #3: cross-reacted with extracts of astrocytoma stage V and with 2 of 16 glioblastoma extracts.
Tissue-associated antigens #1 and #2: shared cross-reactivities with material from the same gel region of separated ductal breast cancer cell membranes, but the antigens were not comparable for precise electrophoretic mobilities.

TABLE 12

In this table the results of two studies of primary and metastatic melanoma TAA are reported.

Study 1: Primary melanoma TAA appeared to be present in some but not all adrenal, lung and liver metastases, and to be absent from many melanoma colon and skin metastases.
Autologous testing of metastatic melanoma TAA showed a different pattern from primary melanoma TAA, but needed further tests for statistical analyses. Positive responses to metastatic melanoma TAA occurred in 47% of patients with Stages I and II and 33% of patients with Stage III or IIIa. This study also suggested that the configuration or structural composition of TAA had altered in some of the metastatic tissues, or was present in complex form.

Study 2: To study the question further, a larger amount of primary tumor of the back and a large amount of metastatic tumor from the same individual were processed, and separated TAA from both sources were tested in 23 nonanergic patients with various stages of melanoma.

10 of 12 (83%) patients with early stage melanoma were positive to primary melanoma TAA 4 of 11 (36%) patients with metastatic melanoma were positive to primary melanoma TAA 5 of 12 (41%) patients with early stage melanoma were positive to metastatic melanoma TAA (two of whom were not positive to primary melanoma TAA)

5 of 11 (45%) patients with metastatic melanoma were positive to metastatic melanoma TAA (one of whom also responded to primary melanoma TAA)

These simultaneous tests of 23 patients also suggested that there might be differences between primary and metastatic TAA.

BOOSTER STUDIES

Subsequent serial skin tests of patients in study 2 produced increased induration responses in previously positive reactors, and conversion to positive responses in six of nine previous nonreactors as well as in five of seven anergic patients not included in the comparative tests.

This suggests that appropriate immunization might serve to strengthen or convert melanoma patients to immunoresponsiveness.

EXAMPLE 10

This example reports the preparation of laryngeal cancer TAA and TAA epitopes:

The tumor-associated antigens for well-differentiated laryngeal squamous cell carcinoma have been identified, isolated, characterized and tested after study of the entire spectrum of membrane antigens from normal, benign and malignant cells isolated from larynx and compared with those from other organs. Three of these antigens are of particular significance in cancer treatment, namely three simple polypeptides which produce positive reactions in laryngeal cancer patient leucocyte migration inhibition tests, in complement fixation tests to sera from the same patients and in controlled, serial skin tests in nonanergic patients for delayed hypersensitivity reactions. Methods used in sequence included the following.

Separated membranes from cells of a well-differentiated laryngeal squamous cell carcinoma are subjected to low frequency sonication and the soluble membrane material further separated by a series of steps involving chromatography, discontinuous gel electrophoresis, isotachophoresis and affinity chromatography. The initial comparison and profile using densitometry of gel profiles was useful in defining proteins for further separation. The initial separation of the soluble membrane protein pool on Sephadex G-200 permitted testing to identify fractions Ib and II for use in further PAGE separations and isotachophoresis purification for characterization studies of single bands. TAA separated further by isotachophoresis was tested in double immunodiffusion electrophoresis against affinity chromatography purified hyperimmune human TAA IgG antibody from patients undergoing specific active TAA immunotherapy. Strong antibodies were present in sera from a patient hyperimmunized for three mos. to TAA and another patient sera taken 10 mos. post-immunization, and both arcs to purified TAA bands in double immunodiffusion electrophoresis were identical.

TABLE 13

Characteristics of well-differentiated laryngeal cancer squamous cell membrane antigens which induce tumor-associated cell-mediated immune responses.

| Purified antigens | Electrophoretic Mobility (cm distance from tracking dye on gradient PAGE) | Chemical composition | Stability in pure form* | | | Migration in relation to proteins of known molecular size** |
|---|---|---|---|---|---|---|
| | | | Room temp. 2 hrs. | 4° C. for 1 week | −70° C. for 6 mos. | |
| TAA[a] | 6.5 | protein | + | + | + | Transferin: migrates 6.4–6.5, 76,500 d |
| HSV-TAA band 1[b] | 3.85 | protein | + | ± | ± | Alpha 1-acid glycoprotein migrates 4.0, 40,000 d |
| HSV-TAA band 2[b] | 3.25 | protein | + | ± | + | Thyroxin-binding prealbumin migrates 3.4, 61,000 d |

[a]Tested for DHR-ST nonanergic 10–14 days postoperative cervical (15/16 positive) and breast cancer patients (0/9) only. This antigen is not as well studied, but is not HSV-related, and is slightly different for each organ sit.
[b]Purified bands are specifically reactive by LMIT, DHR-ST and CF. See reference 6.
Tracking dye is bromphenol blue (670 d); PAGE stacked gels: 3.5, 4.75, 7 and 10%; calculations adjusted for relation of TD to marker albumin in control PAGE.
Staining individual gels with Coomassie brilliant blue, oil red O, periodic acid Schiff.
*As tested by reseparation on SDS-PAGE for intact band and by DHR skin test and LMIT for CMI activity.
**Estimation of precise migration of serum components on control gels; identification of specific components by reactions with monospecific antisera in gel double-diffusion.

As shown in Table 13, the three tumor-associated antigens are all simple polypeptides, two of which are fairly stable at −70° C. after purification and one of which is not as stable after isolation. At that time, an estimation of precise migration of control substances on identical gels, with backup identification of these substances by reactions with monospecific antisera in gel double-diffusion permitted an approximation of the weights of the TAAs.

One of these TAAs is found in slightly different configuration but with shared immunological identity in other squamous cell tumors from different parts of the body and the TAA from laryngeal cancer squamous cell membranes migrated approximately in the same area on stacked discontinuous gradient polyacrylamide SDS gels as the control protein Transferin (Table 13), although of different properties. The other two antigens have been described previously as associated with herpesvirus-induced markers which share partial identity with the tumor antigens delineated for squamous cell cancers. The three antigens are pooled for a polyvalent TAA biological drug for Phase I studies. As shown in Table 13, the three antigens have distinct electrophoretic mobilities and can be semi-purified, hyperimmune antisera to the individual antigens prepared, and then IgG separated to use in affinity chromatography for further purification as well as for development of monospecific antisera to each of the components. The hyperimmune patient sera and the monospecific antisera were used in identification of monoclonal cells from purified TAA-primed mouse-mouse hybridizations for use in the development of epitopes for monitoring and drug-tagging studies.

During the final purification steps of the three laryngeal cancer TAAs, as tested by double immunodiffusion electrophoresis and enzyme immunoassay against affinity-purified hyperimmune human antibodies obtained from patients receiving TAA immunotherapy, it was noted that two antigens, laryngeal TAA (LX-1) and HSV-TAA band 2 (LX-3) were fairly stable at −70° C. but HSV-TAA band 1 (LX-2) was not very stable after isolation. It took several attempts to produce monoclonal antibodies to LX-TAA-2, which in purified form is approximately 37,000d molecular weight. An additional nine monoclonal antibodies to the other two TAAs were produced.

Both Mab and Mab-derived epitopes were tested by enzyme-linked immunosorbent assay against a coded series of 30 non-laryngeal squamous cancer sera, 36 non-squamous cancer sera and 32 laryngeal cancer sera. All positive sera were titered and compared with titered sera from the immunized patient to compare polyclonal and monoclonal reactivities, and an index was used to indicate the strength of reactivity. Shown in Table 14 are the immunoassays of LX-TAA-1 epitopes a62, f18 and i5 which gave 63% cross-reactions with other squamous cancer sera. The three epitopes were combined to produce approximately 50-fold stronger antigenicity in ELISA. Other epitopes were either weak reactors or seen as less specific in the more sensitive enzyme immunoassays. It is possible that anti-idiotype procedures might be useful in developing stronger antigens. An antibody was prepared to f18 epitope which appeared to be a mirror image, but seven other antibodies were not mirror images of the original Mab.

In addition, I have performed serial titrations of immunized patient sera to some of the more reactive epitopes.

TABLE 14

LX-TAA-1 Epitopes versus Non-squamous Cancer, Non-laryngeal Squamous Cancer and Laryngeal Squamous Cancer Sera, as measured by Enzyme Immunoassays.

| Epitopes: | SERA NON-SQUAMOUS | SQUAMOUS CELL CANCERS | |
|---|---|---|---|
| | | Non-larynx | Larynx |
| a62 | 6/36 | 14/30 | 16/32 |
| f18 | 1/36 | 8/30 | 12/32 |
| i5 | 4/36 | 15/30 | 32/32 |
| Number of sera positive to one or more epitopes | 14% (5) | 63% (19) | 100% |

Elisa measurements were made, in which LX-TAA-1 epitope f18 gave strong but very early reactivity at 3-4 months, so that it is useful as a marker for early post-vaccination response. Epitope i5 shows a low titer but continuing positive response beginning at 7 mos. post-vaccination and lasting up to three years.

While the present invention has been described with respect to certain preferred embodiments, including tables and figures used in conjunction therewith, it will be apparent that the invention toward which the present application is directed is not to be limited to any such preferred embodiments, but will include such alterations and modifications thereof as will be obvious to those of ordinary skill in the art. As to all such obvious alterations and modifications, I intend that they be included within the purview of my invention, which is to be limited only by the scope, including equivalents, of the following, appended claims.

What is claimed is:

1. A method of making an epitope of a tumor-associated antigen, which epitope is capable of generating a specific immunotherapeutic response, comprising
   (a) preparing monoclonal antibodies to said TAA,
   (b) coating a matrix with said TAA-specific monoclonal antibodies,
   (c) adding said tumor-associated antigen to said antibody-conjugated matrix to form TAA-Mab complexes on said matrix,
   (d) washing the bound complex to remove impurities therefrom,
   (e) dissociating and eluting the TAA from said complex by an elution buffer,
   (f) dividing said TAA into fragments to a degree less than complete hydrolysis and whereby antigenicity is retained, and some of the fragments contain epitopes having specific reactivity with said monoclonal antibodies,
   (f) adding said TAA fragments to said Mab-conjugated matrix to form complexes between the Mab and fragments possessing the particular epitope defined by the Mab,
   (g) washing the matrix to remove non-epitope containing TAA fragments therefrom, and
   (h) dissociating and eluting the TAA fragments which bound to the Mab, thereby recovering TAA fragments containing the epitope defined by the Mab.

2. A method of making an epitope as claimed in claim 1, in which said tumor-associated antigen has been separated from other protein components according to size by ultrafiltration chromatography.

3. A method of making an epitope as claimed in claim 1, in which said tumor-associated antigen has been separated from other protein components by immunoaffinity chromatography.

4. A method of making an epitope as claimed in claim 1, in which said tumor-associated antigen has been separated from other protein components according to charge by ion exchange chromatography.

5. A method of making an epitope as claimed in claim 1, in which said tumor-associated antigen has been separated from other protein components according to charge by polyacrylamide gel electrophoresis.

6. A method of making an epitope as claimed in claim 1, in which said tumor-associated antigen added to the matrix is ultrapure and has been separated from other protein components by isotachophoresis.

7. A method of making an epitope as claimed in claim 6, in which said ultrapure tumor-associated antigen has been subjected to immunoaffinity chromatography.

8. A method of making an epitope as claimed in claim 1, in which said tumor-associated antigen is divided into fragments by enzymatic action.

* * * * *